United States Patent [19]

Komorn et al.

[11] 4,319,047

[45] Mar. 9, 1982

[54] PREPARATION OF BETA-METHYLTHIOPROPIONALDEHYDE

[75] Inventors: Yves Komorn, Tassin-la-Demi-Lune; Ghislain Schwachhofer, Miribel, both of France

[73] Assignee: Rhone-Poulenc Industries, Paris, France

[21] Appl. No.: 164,539

[22] Filed: Jul. 2, 1980

[30] Foreign Application Priority Data

Jul. 10, 1979 [FR] France ................................ 79 17827

[51] Int. Cl.³ ............................................. C07C 151/00
[52] U.S. Cl. ........................................ 568/41; 568/458
[58] Field of Search ................................... 568/41, 458

[56] References Cited

U.S. PATENT DOCUMENTS 2,626,282  1/1953  Cunningham et al. ................ 568/41
3,574,766  4/1971  Megee ..................................... 568/41
4,225,516  9/1980  Biola ....................................... 568/41

Primary Examiner—Werren B. Lone
Attorney, Agent, or Firm—Burns, Doane, Swecker & Mathis

[57] ABSTRACT

Beta-methylthiopropionaldehyde is prepared by (I) condensing a gaseous feedstream comprising both acrolein and water, advantageously the off-gas resulting from the air oxidation of propylene (and after the acrylic acid content has been absorbed therefrom), to obtain an aqueous condensate containing a fraction of said acrolein and a gaseous acrolein effluent, (II) partially vaporizing said aqueous condensate whereby to obtain a gaseous phase comprising essentially all of said acrolein fraction and a liquid phase comprising essentially no acrolein, (III) recycling said gaseous phase into said gaseous feedstream to be condensed, and (IV) directly reacting said gaseous acrolein effluent with methylmercaptan.

13 Claims, 1 Drawing Figure

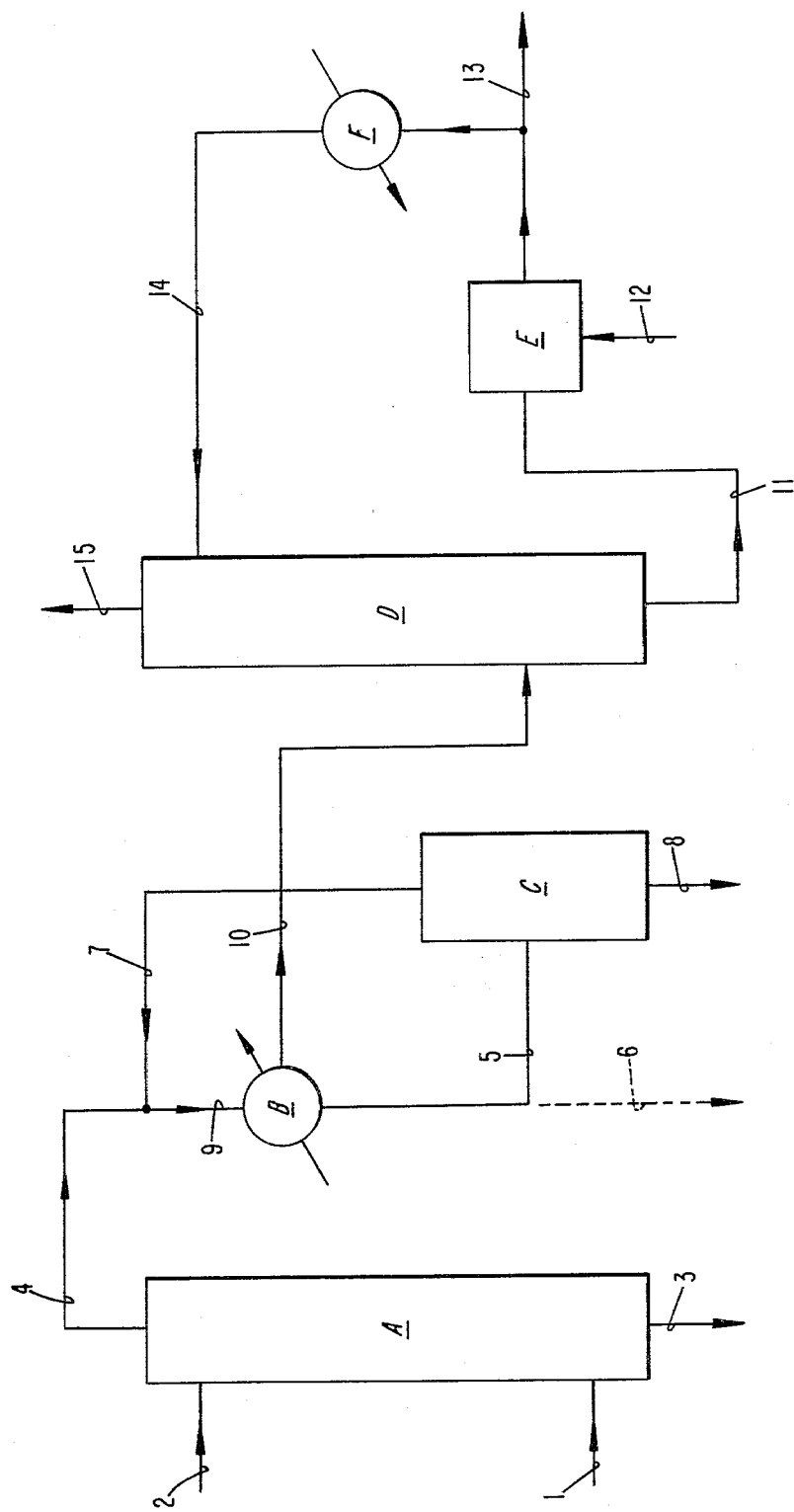

PREPARATION OF BETA-METHYLTHIOPROPIONALDEHYDE

BACKGROUND OF THE INVENTION

1. Field of the Invention

The present invention relates to an improved process for the direct preparation of beta-methylthiopropionaldehyde by reacting methylmercaptan with a gaseous mixture which contains acrolein and which results from the catalytic, air oxidation of propylene in the presence of water.

2. Description of the Prior Art

In copending allowed application, Ser. No. 696,432, filed June 15, 1976, now U.S. Pat. No. 4,225,516, and assigned to the assignee hereof, there is featured a process for the preparation of beta-methylthiopropionaldehyde from methylmercaptan and a gaseous mixture comprising acrolein resulting from the catalytic oxidation of propylene. In accordance with this process, in a first stage, the crude gaseous mixture emanating from the oxidation reactor is charged into an absorption column wherein the acrylic acid present in the gaseous mixture is removed; in a second stage, the gaseous mixture no longer containing acrylic acid is condensed so as to remove the water present therein. After such removal of both the acrylic acid and the water, the gaseous mixture containing acrolein absorbed in beta-methylthiopropionaldehyde is reacted with methylmercaptan to provide beta-methylthiopropionaldehyde.

The main disadvantage of this type of process is that, during the condensation operation for the purpose of removing the water present in the gaseous mixture, it is physically impossible not to condense, at the same time, some of the acrolein present in the gaseous mixture. Thus, such operation affords an aqueous solution containing from 10 to 20% of the acrolein formed during the oxidation of propylene.

In order to avoid losing this appreciable amount of acrolein, it becomes necessary to separate it from the aqueous solution, preferably by distillation, and to reintroduce or recycle same into the third stage mentioned above, namely, the stage involving the reaction of the methylmercaptan with the acrolein.

This separation and reintroduction or recycling entail an isolation process and hence the collection of a mass of virtually pure acrolein, and this flies in the face of the very spirit of the process, the object of which being to prepare beta-methylthiopropionaldehyde without the necessity for an intermediate isolation of the acrolein. In fact, this is of great practical importance, in particular on an industrial scale, because it is well known to those skilled in the art that acrolein is a toxic material, the handling of which involves numerous risks and which has been the cause of numerous serious environmental accidents.

Furthermore, the recycling of a stream of concentrated acrolein together with the dilute gas stream, in the step involving reaction with the methylmercaptan, is complicated by the fact that, according to the aforementioned patent application, it is imperative to conduct the reaction within strict limits vis-a-vis the acrolein/methylmercaptan stoichiometry; in fact, the hemithioacetal concentration within the reaction mixture should be permanently maintained between 0 and 1%, the value 0 being excluded.

SUMMARY OF THE INVENTION

Accordingly, a major object of the present invention is the provision of an improved process for the preparation of beta-methylthiopropionaldehyde from an acrolein-containing, propylene oxidation off-gas, which process does not entail the separation of a distinct mass of pure liquid acrolein, but which nonetheless still results in high yields of beta-methylthiopropionaldehyde, relative to the acrolein present in the crude gas stream originating from the propylene oxidation reactor.

Briefly, this invention features a process for the direct preparation of beta-methylthiopropionaldehyde, in accordance with which (i) in a first step, the acrylic acid present in the crude gas stream emanating from the catalytic oxidation of propylene with air is removed by absorption of the said crude gas stream in water or in a solvent, (ii) in a second step, the water present in the gas stream effluent from the first step is removed by condensation of the said stream, and (iii) in a third step, the gaseous mixture deriving from said second step is reacted with methylmercaptan in order to form the beta-methylthiopropionaldehyde; said process being characterized in that (iv) the liquid mixture effluent from the second step and essentially consisting of water and acrolein is partially vaporized such as to provide a gas phase containing virtually all of the acrolein and a liquid phase containing virtually no acrolein, and in that the said gas phase containing virtually all of the acrolein is recycled into the said gas steam effluent from the first absorption step, upstream of the second condensation step.

BRIEF DESCRIPTION OF THE DRAWING

The FIGURE of Drawing is a schematic/diagrammatic representation of one apparatus train suitable for carrying out the process according to the invention.

DETAILED DESCRIPTION OF THE INVENTION

More particularly, according to the invention, the catalytic oxidation of propylene by air can be carried out in accordance with any of the various processes per se well known to the prior art. In particular, a mixture of propylene, air and water can be passed through a tubular reactor, the temperature of which is controlled by a heat-exchange fluid, and which contains a catalyst based upon the oxides of cobalt, molybdenum, iron and bismuth (a catalyst of this type is described in U.S. Pat. No. 4,166,808, also assigned to the assignee hereof).

Regardless of the process used, the gas stream emanating from the oxidation reactor contains acrolein, water and acrylic acid as the main condensable products.

The water and the acrylic acid must be removed in order to avoid the degradation reactions which give rise to a considerable reduction in the yield of the desired beta-methylthiopropionaldehyde.

In order to remove the acrylic acid, the gas stream emanating from the oxidation reactor can be passed, in a manner which is in and of itself known, through an absorption column charged with water (as described in French Pat. No. 1,393,175) or with a solvent, such as tributyl phosphate (as described in U.S. Pat. No. 3,555,082) or, for example, a mixture of biphenyl and diphenyl ether (French Pat. No. 2,146,386).

The solution of acrylic acid can then be treated in order to recover the pure acrylic acid, as described in copending allowed application Ser. No. 914,923, filed June 12, 1978 and also assigned to the assignee hereof.

When this operation for the removal of the acrylic acid has been completed, the water is removed, also in a manner which is in and of itself known, by condensing, at low temperature, the gas stream exiting the aforementioned absorption column. The outlet temperature of the condenser or condensers employed is advantageously between 0° and 10° C.

According to a first embodiment of this invention, the liquid mixture effluent from the condensation step, which mixture essentially consists of water and acrolein, is subjected to partial vaporization. As utilized herein, by the expression "partial vaporization" there is intended a separation into two phases, namely, an aqueous phase no longer containing acrolein and a gas phase containing all of the acrolein which has been condensed in the condensation step.

According to a second embodiment of the invention, the gas phase obtained as described above is recycled into the gas stream obtained from the first step, i.e., that involving the absorption of the acrylic acid, before it enters, or upstream of the condenser or condensers.

The partial vaporization is preferably carried out at a temperature between about 70° C. and about 130° C., under an absolute pressure between about 0.8 bar and about 3 bars. According to a preferred embodiment of the invention, the partial vaporization of the liquid mixture obtained after condensation is carried out in a "flash distillation" apparatus, which too is in and of itself well known and which ensures, with but short residence time, a distillation corresponding to a single theoretical stage.

According to a second preferred embodiment of the invention, the partial vaporization of the liquid mixture is carried out in a stripping distillation apparatus, namely, a distillation column in which the liquid feed takes place in the upper part, the lower stages stripping the acrolein out of the mixture.

According to a third preferred embodiment of the invention, an apparatus for stripping by means of a gas is used. For example, the liquid mixture can be fed into the top of a column, a heated gas (for example, nitrogen or steam) being counter-currently introduced into the bottom of the column.

According to a fourth preferred embodiment of the invention, a rotary or non-rotary thin film evaporator is used.

It will be apparent that the invention also envisages the case in which any combination of the four devices described above is used in series.

Consistent with the invention, an aqueous solution no longer containing acrolein is thus obtained at the outlet of the partial vaporization apparatus. In this way, any storage and any handling of acrolein in concentrated and liquid form is avoided.

The gaseous mixture effluent from the condenser or condensers is then reacted with methylmercaptan in a manner per se known. The reaction can be carried out as described, for example, in the aforesaid copending application Ser. No. 696,432, namely, by proceeding as follows: the gaseous mixture deriving from the condenser or condensers is introduced into the base of an adsorption column, the top of which being charged with the beta-methylthiopropionaldehyde. The effluent from this column (namely, acrolein absorbed in the beta-methylthiopropionaldehyde) is conveyed to a reactor into which the methylmercaptan and the catalyst (for example, triethylamine) are introduced. A fraction of the beta-methylthiopropionaldehyde produced is drawn off, the remainder being cooled and then recycled into the top of the absorption column, with the waste gases being removed from the top of this column. According to said copending application Ser. No. 696,432, a concentration of intermediate hemithioacetal of between 0 (excluding 0) and 1% is maintained in the reaction medium.

It too is apparent that this invention is applicable to any alternative in which the gaseous mixture exiting the condenser or condensers would be reacted with the methylmercaptan in accordance with a process different from that earlier described.

In order to further illustrate the present invention and the advantages thereof, the following specific examples are given, it being understood that same are intended only as illustrative and in nowise limitative.

EXAMPLE 1

This example is illustrative of the process according to the invention, with reference to the accompanying FIGURE of Drawing, in the context of an isolated operation for partial vaporization from an initial condensate.

The gaseous effluent 1 deriving from the catalytic oxidation of propylene by air in the presence of water had the following composition (in mols):

| Inert gases | 547 |
|---|---|
| Water | 395 |
| Acrolein | 49.6 |
| Acrylic Acid | 6 |
| Acetaldehyde and other compounds | 2.4 |

This effluent, which was at a temperature of 350° C., was charged into an absorption column A which too was charged, via line 2, with a feedstream of tributyl phosphate at a temperature of 50° C. A solution of acrylic acid and tributyl phosphate, and containing trace amounts of water and acrolein, was collected at outlet 3.

The gas stream 4, which exited the top of the column A at 80° C., had the following composition:

| Inert gases | 547 |
|---|---|
| Water | 392 |
| Acrolein | 49.2 |
| Acrylic acid | 0.06 |
| Acetaldehyde and other compounds | 2 | and was fed into a condenser B in which it was cooled to 0° C.

According to prior art techniques, the liquid mixture effluent from the condenser B was recovered at 6 and separately treated in order to recover the acrolein present therein. The gaseous mixture was conveyed directly to the operation involving reaction with methylmercaptan. The compositions of these two mixtures are reported in Table 1 below:

TABLE 1

| Mixture | 6 | 10 |
|---|---|---|
| Inert gases | 0 | 547 |
| Water | 389.7 | 2.3 |
| Acrolein | 7.2 | 42 |

TABLE 1-continued

| Mixture | 6 | 10 |
|---|---|---|
| Acrylic acid | 0.06 | 0 |
| Acetaldehyde and other compounds | 0.5 | 1.5 |

The improvement provided by the process according to the invention consisted in introducing the liquid mixture 6, via line 5, into the apparatus C which, in this embodiment, included two flash distillation stages operating, respectively, at temperatures of 97° and 100° C. under atmospheric pressure.

This partial vaporization in two stages produced, on the one hand, an aggregate of two gas phases which, when combined formed the mixture 7 which was intended to be recycled upstream of the condenser B, and, on the other hand, an aqueous liquid phase 8 containing only traces of acrolein, of acrylic acid and of other compounds, consistent with the compositions given in Table 2:

TABLE 2

| Mixture | 6 | 7 | 8 |
|---|---|---|---|
| Inert gases | 0 | 0 | 0 |
| Water | 398.7 | 102.5 | 287.2 |
| Acrolein | 7.1 | 7.15 | 0.05 |
| Acrylic acid | 0.06 | — | 0.06 |
| Acetaldehyde and other compounds | 0.5 | — | 0.5 |

If the condensation, the partial vaporization and the recycling upstream of the condenser B are carried out simultaneously in a continuous process, it is clear that an equilibrium will be established as regards a permanent and constant amount of acrolein condensed and then revaporized in a more concentrated form, while virtually all of the acrolein produced and charged via the line 4 will remain in the gas state in the outlet stream 10 proceeding to the reaction with methylmercaptan.

Furthermore, also according to the invention, there no longer remains any acrolein to be separated off in a liquid and concentrated form, which would require a complementary reaction with methylmercaptan. In fact, consistent with the prior art, the acrolein condensed with the water was recovered in a conventional manner, namely, typically by distillation, and this produced an azeotrope which consisted of acrolein containing about 3% water; this concentrated acrolein could in turn be reacted with methylmercaptan.

EXAMPLE 2

The process was carried out continuously as in Example 1, but, in this event, and also with reference to the accompanying FIGURE of Drawing, the apparatus C was a stripping column, with the feed thereto being onto the upper plate, which was at 83° C. under an absolute pressure of 1.5 atmospheres.

The gaseous mixture 10 was introduced into an absorption column D which was top fed with beta-methylthiopropionaldehyde. The acrolein absorbed in the beta-methylthiopropionaldehyde was charged into the reactor E, into which the catalyst (triethylamine; 0.05% of the reaction mixture) and the methylmercaptan (molar flow rate of 49.3 mols) were also introduced. At the outlet of the reactor, some of the beta-methylthiopropionaldehyde produced was drawn off at outlet 13, while the initial excess fraction 14 was cooled (F) to a temperature of −10° C. and then recycled to the top of the column D, from which the waste gases exited at 15.

The molar flow rates in the various feed and outlet lines are reported in Table 3 below:

TABLE 3

| Composition (in mols) | 1 | 4 | 9 | 5 | 7 | 8 | 10 | 15 | 13 |
|---|---|---|---|---|---|---|---|---|---|
| Inert gases | 547 | 547 | 547 | | | | 547 | 547 | |
| Water | 395 | 392 | 398 | 396 | 6 | 390 | 2 | — | 2 |
| Acrolein | 49.6 | 49.2 | 59.9 | 10.75 | 10.7 | 0.05 | 49.15 | — | — |
| Acrylic acid | 6 | 0.06 | 0.06 | 0.06 | — | 0.06 | — | — | — |
| Acetaldehyde and other compounds | 2.4 | 2 | 2.2 | 0.7 | 0.2 | 0.5 | 1.5 | 1.5 | 0.4 |
| Beta-methyl-thiopropion-aldehyde | — | — | — | — | — | — | — | 0.15 | 48.7 |

It was determined that 99.5% of the acrolein introduced via the line 4 was collected in the vapor state, in the line 10, in the gaseous mixture introduced into the absorption column D.

A comparison of the composition of the line 10 in Table 1 of Example 1 (prior art) with the composition of the line 10 in Table 3 below (this invention) clearly evidences the advantage provided by the process of the invention (42 mols of gaseous acrolein are present in the feedstream 10 of the prior art, while 49.2 mols are present in the feedstream 10 per the invention, the same amount of acrolein being present in the line 4).

The beta-methylthiopropionaldehyde obtained in accordance with the process of the invention is useful, in particular, as an intermediate in the synthesis of methionine utilized in animal feeds.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of beta-methylthiopropionaldehyde which comprises (I) condensing a gaseous feedstream (i) comprising both acrolein and water to obtain an aqueous condensate (ii) containing a fraction of said acrolein and a gaseous acrolein effluent (iii) and (II) directly reacting said acrolein in said effluent (iii) with methylmercaptan to yield beta-methylthiopropionaldehyde, the improvement comprising partially vaporizing said aqueous condensate (ii) to obtain a gaseous phase (iv) comprising essentially all of said acrolein fraction in said condensate and a liquid phase (v) comprising essentially no acrolein, and recycling said gaseous phase (iv) into said gaseous feedstream (i) to be condensed.

2. The process as defined by claim 1, said gaseous feedstream (i) comprising the off-gas from the air oxidation of propylene.

3. The process as defined by claim 2, comprising preliminarily absorbing any acrylic acid present from said off-gas prior to said condensing step (I).

4. The process as defined by claim 3, said absorption being effected with a member selected from the group consisting of water and an acrylic acid solvent.

5. The process as defined by claim 4, said off-gas emanating from the catalytic air oxidation of propylene, in the presence of water, and comprising the condensables acrolein, water and acrylic acid.

6. The process as defined by claim 4, said partial vaporization being conducted at a temperature of from 70° C. to 130° C.

7. The process as defined by claim 6, said partial vaporization being conducted at a pressure of from about 0.8 bar to about 3 bars.

8. The process as defined by claim 4, said partial vaporization being effected by flash distillation.

9. The process as defined by claim 4, said partial vaporization being effected by strip distillation.

10. The process as defined by claim 4, said partial vaporization being effected by countercurrent gas/liquid contact.

11. The process as defined by claim 4, said partial vaporization being effected by thin film evaporation.

12. The process as defined by claim 4, said acrolein in said effluent (iii) being absorbed in beta-methylthiopropionaldehyde prior to reaction with the methylmercaptan.

13. The process as defined by claim 4 or 12, the acrolein/methylmercaptan reaction mixture comprising an amount of hemithioacetal, in a concentration of 1% or less.

* * * * *